United States Patent
Inoue et al.

(10) Patent No.: US 9,573,881 B2
(45) Date of Patent: Feb. 21, 2017

(54) HALOGENATED ANILINE AND METHOD FOR PRODUCING SAME

(71) Applicant: Nippon Soda Co., Ltd., Chiyoda-ku, Tokyo (JP)

(72) Inventors: Hiroki Inoue, Takaoka (JP); Yuzuru Sakata, Takaoka (JP); Shinichi Kobayashi, Takaoka (JP); Yoshikazu Ito, Takaoka (JP); Takashi Kitayama, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/652,913

(22) PCT Filed: Dec. 20, 2013

(86) PCT No.: PCT/JP2013/084300
§ 371 (c)(1),
(2) Date: Jun. 17, 2015

(87) PCT Pub. No.: WO2014/103947
PCT Pub. Date: Jul. 3, 2014

(65) Prior Publication Data
US 2015/0329472 A1    Nov. 19, 2015

(30) Foreign Application Priority Data
Dec. 25, 2012 (JP) .................. 2012-280691

(51) Int. Cl.
| C07C 209/74 | (2006.01) |
| C07C 17/00 | (2006.01) |
| C07C 201/14 | (2006.01) |
| C07C 209/32 | (2006.01) |
| C07C 205/12 | (2006.01) |
| C07C 211/52 | (2006.01) |
| C07C 17/12 | (2006.01) |

(52) U.S. Cl.
CPC ............ *C07C 209/74* (2013.01); *C07C 17/00* (2013.01); *C07C 17/12* (2013.01); *C07C 201/14* (2013.01); *C07C 205/12* (2013.01); *C07C 209/32* (2013.01); *C07C 211/52* (2013.01)

(58) Field of Classification Search
None
See application file for complete search history.

(56) References Cited

U.S. PATENT DOCUMENTS

| 5,091,580 A | 2/1992 | Pews et al. |
| 5,498,794 A | 3/1996 | Schach et al. |
| 2010/0317675 A1 | 12/2010 | Peyronel |
| 2012/0178931 A1 | 7/2012 | Kawazoe |
| 2012/0289702 A1 | 11/2012 | Shibayama et al. |

FOREIGN PATENT DOCUMENTS

| CN | 101245020 A | 8/2008 |
| CN | 101811973 A | 8/2010 |
| CN | 102030616 A | 4/2011 |
| EP | 0224001 A1 | 6/1987 |
| JP | 62-181243 A | 8/1987 |
| JP | 02-286636 A | 11/1990 |
| JP | 04-178355 A | 6/1992 |
| JP | 07-048321 A | 2/1995 |
| JP | 07-309815 A | 11/1995 |
| JP | 2003-507462 A | 2/2003 |
| JP | 2007-536224 A | 12/2007 |
| JP | 2010-026024 A | 2/2010 |
| WO | WO 01/14354 A1 | 3/2001 |
| WO | WO 2005/112932 A3 | 12/2005 |
| WO | WO 2006/129064 A1 | 12/2006 |
| WO | WO 2009/029592 A1 | 3/2009 |
| WO | WO 2009/045992 A2 | 4/2009 |
| WO | WO 2009/106750 A2 | 9/2009 |
| WO | WO 2010/091272 A1 | 8/2010 |
| WO | WO 2011/024429 A1 | 3/2011 |
| WO | WO 2011/081174 A1 | 7/2011 |

OTHER PUBLICATIONS

Registry (STN) [online], Jun. 7, 2013, retrieval date Mar. 5, 2014, CAS registry No. 1435806-67-9, one page.
International Search Report dated Mar. 18, 2014, in PCT/JP2013/084300.
Cervena et al., "Fluorinated tricyclic neuroleptics: 6,7-difluoro derivative of chlorprothixene and 2-fluoro-3-hydroxy derivative of octoclothepin," Collection of Czechoslovak Chemical Communications, 1977, 42(6):2001-2017.
Paterson et al., "Determination of relative signs of H—F coupling constants in fluorobenzenes by nuclear magnetic double resonance," Canadian Journal of Chemistry, 1963, 41(10):2706-2709.
Registry (STN) [online], Jun. 7, 2013, retrieval date Mar. 5, 2014, CNS registry No. 1435806-67-9, one page.
Weigert et al., "Synthesis and aromatization of 2+2 cycloadducts of butadienes and tetrafluoroethylene," Journal of Fluorine Chemistry, 1993, 63(1-2):69-84.

*Primary Examiner* — Clinton Brooks
(74) *Attorney, Agent, or Firm* — Foley & Lardner LLP

(57) ABSTRACT

The present invention provides a halogenated aniline represented by formula (I) (wherein each of $X^1$ and $X^2$ independently represents a chlorine atom, a bromine atom or an iodine atom), a method for producing the halogenated aniline, and other aspects.

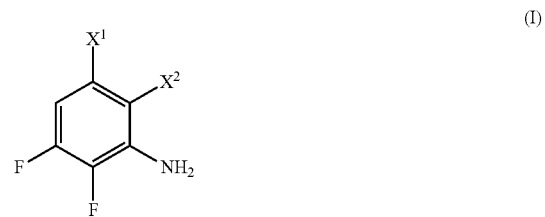

(I)

6 Claims, No Drawings

HALOGENATED ANILINE AND METHOD FOR PRODUCING SAME

TECHNICAL FIELD

The present invention relates to a novel halogenated aniline, which can be used as a production raw material for compounds that are useful as electronic materials, medicines, and agricultural chemicals and the like, as well as a method for producing the halogenated aniline.

Priority is claimed on Japanese Patent Application No. 2012-280691, filed Dec. 25, 2012, the content of which is incorporated herein by reference.

BACKGROUND ART

The compound 2,3-difluoroaniline is the starting raw material for producing 2-[2-fluoro-6-(7,8-difluoro-2-methylquinolin-3-yloxy)phenyl]propan-2-ol and 2-[2-fluoro-6-(7,8-difluoroquinolin-3-yloxy)phenyl]propan-2-ol, which are known as active ingredients for agricultural and horticultural germicides (Patent Document 1).

Further, 2,3-difluoroaniline is also used in the production of medicines such as antibiotics (Patent Document 2), c-Met protein kinase inhibitors (Patent Document 3), drugs for Alzheimer's disease (Patent Document 4), Aurora 13 kinase inhibitors (Patent Document 5), and drugs for neuropathic pain (Patent Document 6).

Moreover, 2,3-difluoroaniline is also used in the production of electronic materials such as the azo compounds contained in compositions for anisotropic films that exhibit high dichroism, which are useful in the polarizing plates and the like fitted to display elements such as liquid crystal display elements (LCD) and organic electroluminescent display elements (OLED) (Patent Document 7).

In this manner, 2,3-difluoroaniline is useful as a production raw material for electronic materials, medicines and agricultural chemicals, and a simple method for producing 2,3-difluoroaniline cheaply and in large quantities has been keenly sought.

One example of a known method for producing 2,3-difluoroaniline involves fluorinating 2,3-dichloronitrobenzene to obtain 3-chloro-2-fluoronitrobenzene, hydrogenating the 3-chloro-2-fluoronitrobenzene to obtain 3-chloro-2-fluoroaniline, using the Schiemann reaction to convert the 3-chloro-2-fluoroaniline to 2,3-difluorochlorobenzene, and then performing an amination reaction with a copper catalyst to produce 2,3-difluoroaniline (Patent Document 8).

[Chemical Formula 1]

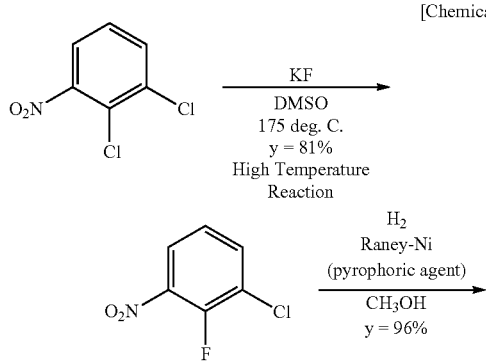

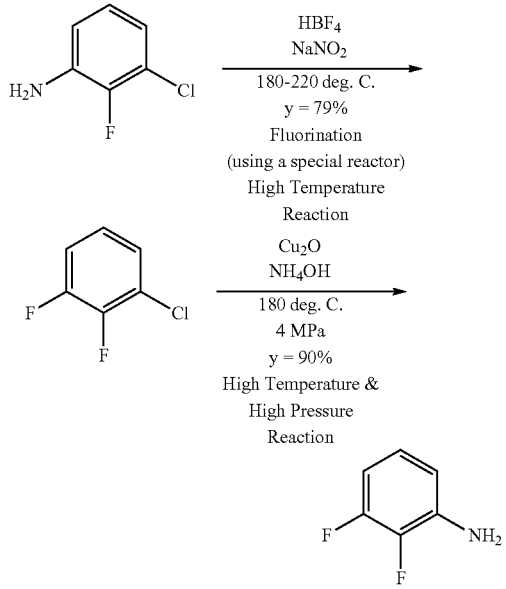

This method requires high temperature and high pressure in the fluorination reaction and the amination reaction, and uses chemical reagents that are difficult to handle such as Raney nickel, and can therefore not really be claimed to be an industrially useful method.

Patent Document 9 discloses that 2,3-difluoroaniline can be obtained by fluorinating 1,2,3-trichlorobenzene to obtain 2,3-difluorochlorobenzene, and then aminating the 2,3-difluorochlorobenzene using a copper catalyst.

[Chemical Formula 2]

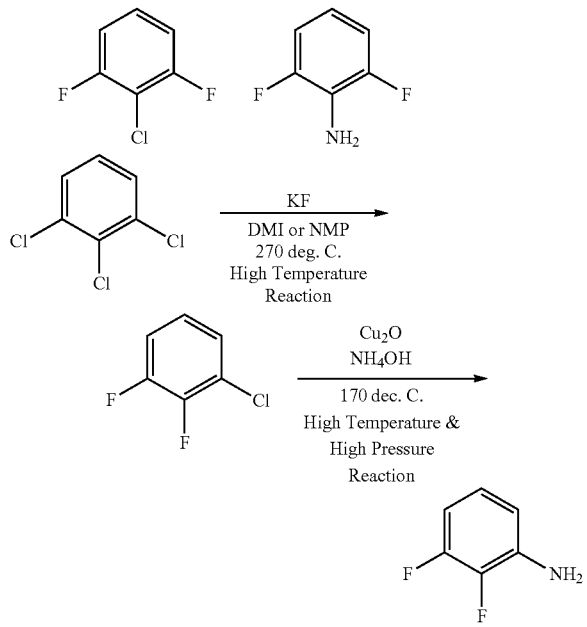

However, in this method, a regioisomer (2,6-difluorochlorobenzene) is produced as a by-product during the fluorination, and therefore the yield of 2,3-difluorochlorobenzene is low. Further, the separation of the 2,3-difluorochlorobenzene from the by-product regioisomer is extremely difficult.

Moreover, high temperature and high pressure conditions are required in the fluorination and amination reactions, meaning this method can also not be claimed to be industrially useful.

Patent Document 10 discloses a method for producing 2,3-difluoroaniline by hydrogenating 2,3-difluoronitrobenzene at high pressure.

[Chemical Formula 3]

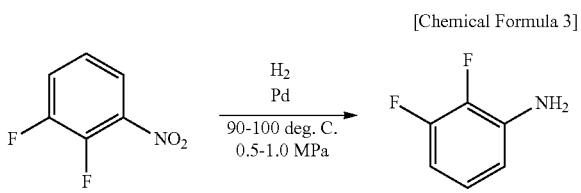 [SMILES: O=[N+]([O-])c1cccc(F)c1F ; "90-100 deg. C.0.5-1.0 MPa" ; Nc1cccc(F)c1F]

This method is simple, having only one step, and is industrially feasible, but the raw material 2,3-difluoronitrobenzene is extremely difficult to obtain, and the only known method in the literature involves oxidation of the target material 2,3-difluoroaniline.

Patent Document 11 discloses a method for producing 2,3-difluoroaniline by hydrogenating 2,3-difluoro-4-chloro-nitrobenzene. However, in this method also, the raw material 2,3-difluoro-4-chloro-nitrobenzene is extremely difficult to obtain.

As described above, currently known methods for producing 2,3-difluoroaniline require high temperature and high pressure reactions, and not only are the equipment costs high due to the requirement for special production equipment, but safety and stability operations are also a significant burden.

PRIOR ART LITERATURE

Patent Documents

Patent Document 1: WO2011/081174
Patent Document 2: WO2010/091272
Patent Document 3: WO2009/045992
Patent Document 4: WO2009/106750
Patent Document 5: WO2006/129064
Patent Document 6: WO2009/029592
Patent Document 7: JP 2010-026024 A
Patent Document 8: CN 101245020
Patent Document 9: U.S. Pat. No. 5,091,580
Patent Document 10: CN 101811973
Patent Document 11: JP 07-309815 A

DISCLOSURE OF INVENTION

Problems to be Solved by the Invention

An object of the present invention is to provide a novel halogenated aniline that can be used to produce 2,3-difluoroaniline and the like via a simple process that avoids the requirement for high temperature and high pressure conditions, 2,3-difluoroaniline being a production raw material for 2-[2-fluoro-6-(7,8-difluoro-2-methylquinolin-3-yloxy)phenyl]propan-2-ol and 2-[2-fluoro-6-(7,8-difluoroquinolin-3-yloxy)phenyl]propan-2-ol and the like, which are useful as agricultural and horticultural germicides that can be used safely and with reliable effect. Another object of the invention is to provide a simple method for producing the halogenated aniline cheaply and in large quantities.

Means for Solving the Problems

The inventors of the present invention conducted intensive investigations aimed at achieving the above objects. As a result, they discovered a novel halogenated aniline that could be used to produce 2,3-difluoroaniline via a simple process that avoided the requirement for high temperature and high pressure conditions. Further, they also discovered a method for producing the novel halogenated aniline of the present invention which avoided high temperature and high pressure conditions and enabled the halogenated aniline to be produced cheaply, simply and in large quantities, by using 1,2-difluorobenzene as the starting raw material, halogenating this 1,2-difluorobenzene, nitrating the thus obtained 1,2-difluoro-4,5-dihalogenobenzene to produce a halogenated nitrobenzene containing a novel halogenated nitrobenzene of the present invention, and then reducing the halogenated nitrobenzene to produce the novel halogenated aniline of the present invention. Furthermore, they also discovered a method for producing 2,3-difluoroaniline which avoided high temperature and high pressure conditions and enabled the 2,3-difluoroaniline to be produced cheaply, simply and in large quantities, by reducing and dehalogenating the halogenated nitrobenzene containing the novel halogenated nitrobenzene of the present invention. The present invention was completed by conducting further investigations based upon these findings.

In other words, the present invention includes the aspects described below.

[Chemical Formula 4]

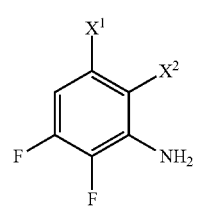

(I)

In formula (I), each of $X^1$ and $X^2$ independently represents a chlorine atom, a bromine atom or an iodine atom.

[Chemical Formula 5]

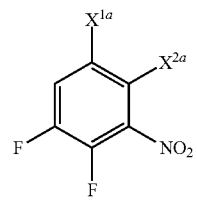

(IIa)

In formula (IIa), each of $X^{1a}$ and $X^{2a}$ independently represents a chlorine atom, a bromine atom or an iodine atom, but the case in which $X^{1a}$ and $X^{2a}$ both represent bromine atoms is excluded.

[Chemical Formula 6]

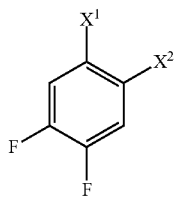
(III)

In formula (III), each of $X^1$ and $X^2$ independently represents a chlorine atom, a bromine atom or an iodine atom.

[Chemical Formula 7]

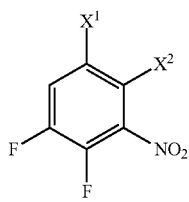
(II)

In formula (II), each of $X^1$ and $X^2$ independently represents a chlorine atom, a bromine atom or an iodine atom.
[1] A halogenated aniline represented by formula (I).
[2] A halogenated nitrobenzene represented by formula (IIa).
[3] A method for producing 2,3-difluoroaniline, including:
a step of halogenating 1,2-difluorobenzene or a 1-halogeno-3,4-difluorobenzene to obtain a halogenated benzene represented by formula (III),
a step of nitrating the halogenated benzene to obtain a halogenated nitrobenzene represented by formula (II),
a step of reducing the halogenated nitrobenzene to obtain a halogenated aniline represented by formula (I), and
a step of subsequently dehalogenating the halogenated nitrobenzene.
[4] The method for producing 2,3-difluoroaniline disclosed above in [3], wherein the 1,2-difluorobenzene or 1-halogeno-3,4-difluorobenzene is halogenated using a Lewis acid catalyst.
[5] A method for producing a halogenated nitrobenzene, including:
a step of halogenating 1,2-difluorobenzene or a 1-halogeno-3,4-difluorobenzene to obtain a halogenated benzene represented by formula (III), and
a step of subsequently nitrating the halogenated benzene to obtain a halogenated nitrobenzene represented by formula (II).
[6] The method for producing a halogenated nitrobenzene disclosed above in [5], wherein fuming sulfuric acid and concentrated nitric acid are added to the halogenated benzene represented by formula (III) to nitrate the halogenated benzene.
[7] The method for producing a halogenated nitrobenzene disclosed above in [5], wherein fuming sulfuric acid and fuming nitric acid are added to the halogenated benzene represented by formula (III) to nitrate the halogenated benzene.
[8] A method for producing a halogenated aniline, including a step of reducing a halogenated nitrobenzene represented by formula (II) to obtain a halogenated aniline represented by formula (I).

[9] A method for producing 2,3-difluoroaniline, including a step of dehalogenating a halogenated aniline represented by formula (I).
[10] A method for producing 2,3-difluoroaniline, including:
a step of reducing a halogenated nitrobenzene represented by formula (II) to obtain a halogenated aniline represented by formula (I), and
a step of dehalogenating the halogenated aniline.
[11] A method for producing 1,2-dichloro-4,5-difluorobenzene, including a step of chlorinating 1,2-difluorobenzene.

Effects of the Invention

The halogenated aniline according to the present invention can be used to easily produce 2,3-difluoroaniline, which is a production raw material for 2-[2-fluoro-6-(7,8-difluoro-2-methylquinolin-3-yloxy)phenyl]propan-2-ol or 2-[2-fluoro-6-(7,8-difluoroquinolin-3-yloxy)phenyl]propan-2-ol or the like. Further, by using the production method of the present invention, the halogenated aniline can be produced cheaply, easily, and in large quantities.

BEST MODE FOR CARRYING OUT THE INVENTION

The halogenated aniline according to the present invention is a compound represented by formula (I). In formula (I), each of $X^1$ and $X^2$ independently represents a chlorine atom, a bromine atom or an iodine atom.

Specific examples of the halogenated aniline according to the present invention include 2,3-dichloro-5,6-difluoroaniline, 2,3-dibromo-5,6-difluoroaniline, 3-bromo-2-chloro-5,6-difluoroaniline, 2-bromo-3-chloro-5,6-difluoroaniline, 2-chloro-3-iodo-5,6-difluoroaniline, and 2-iodo-3-chloro-5,6-difluoroaniline.

The halogenated nitrobenzene according to the present invention is a compound represented by formula (IIa). In formula (IIa), each of $X^{1a}$ and $X^{2a}$ independently represents a chlorine atom, a bromine atom or an iodine atom. However, the case in which $X^{1a}$ and $X^{2a}$ both represent bromine atoms is excluded.

Specific examples of the halogenated nitrobenzene according to the present invention include 1,2-dichloro-4,5-difluoro-3-nitrobenzene, 1-bromo-2-chloro-4,5-difluoro-3-nitrobenzene, 2-bromo-1-chloro-4,5-difluoro-3-nitrobenzene, 1-iodo-2-chloro-4,5-difluoro-3-nitrobenzene, and 1-chloro-2-iodo-4,5-difluoro-3-nitrobenzene.

The halogenated aniline represented by formula (I) according to the present invention can be produced using 1,2-difluorobenzene or a 1-halogeno-3,4-difluorobenzene as the starting raw material, by performing the three steps described below.

The first step is a step of halogenating 1,2-difluorobenzene or a 1-halogeno-3,4-difluorobenzene to produce a halogenated benzene represented by formula (III). In formula (III), each of $X^1$ and $X^2$ independently represents a chlorine atom, a bromine atom or an iodine atom.

The halogenation of the first step can be conducted under the type of halogenation conditions widely used in typical organic chemical synthesis reactions. Examples of halogenating agents that can be used include molecular chlorine, molecular bromine, molecular iodine, sulfuryl chloride, sulfuryl bromide, N-chlorosuccinimide, N-bromosuccinimide, 1,3-dibromo-5,5-dimethylhydantoin, and 1,3-diiodo-5,5-dimethylhydantoin. Among these compounds, the use of molecular chlorine or molecular bromine is preferable.

The halogenation of 1,2-difluorobenzene preferably employs a catalyst. The catalyst is preferably a Lewis acid catalyst such as Fe, $FeCl_3$, $FeBr_3$, $Fe_2O$, Al, $Al_2O_3$, $AlCl_3$, a zeolite, $ZrO_2$, $SbCl_3$, $SbCl_5$, $TiCl_4$, $SnCl_4$ or $MoCl_5$. Among these, Fe, $FeCl_3$ or $FeBr_3$ is more preferable, and Fe is particularly desirable.

The amount used of the catalyst, relative to the mass of the 1,2-difluorobenzene raw material, is preferably from 0.1 to 50% by mass, and more preferably from 0.5 to 10% by mass. Alternatively, any of various sulfur compounds may be added as co-catalysts for the purpose of altering the reaction selectivity or the reaction rate.

The reaction temperature may be set within a range from −40 to 200° C., but if smooth progression of the reaction and the boiling point of the raw material are taken into consideration, then the reaction temperature is preferably from 0 to 70° C., and more preferably from 40 to 60° C. The reaction is usually performed in the absence of a solvent, but a solvent that is inert during the halogenation, such as carbon tetrachloride, chloroform, carbon disulfide or acetic acid, may be used if necessary.

The second step is a step of nitrating the halogenated benzene represented by formula (III) to produce a halogenated nitrobenzene represented by formula (II). In formula (II), each of $X^1$ and $X^2$ independently represents a chlorine atom, a bromine atom or an iodine atom.

The nitration of the second step may employ typical nitration methods widely used in organic chemical synthesis reactions. Examples of methods that may be used include nitration in a mixed acid system using at least one of concentrated nitric acid, a nitrate salt and fuming nitric acid, and at least one of concentrated sulfuric acid and fuming sulfuric acid, nitration in glacial acetic acid or acetic anhydride solvent, and nitration in a fuming nitric acid system.

The above-mentioned nitration in a mixed acid system is preferably:

a method in which the nitration is performed by adding fuming sulfuric acid and fuming nitric acid to the halogenated benzene represented by formula (III), a method in which the nitration is performed by adding fuming sulfuric acid and a nitrate salt to the halogenated benzene represented by formula (III), a method in which the nitration is performed by adding concentrated sulfuric acid and fuming nitric acid to the halogenated benzene represented by formula (III), or a method in which the nitration is performed by adding fuming sulfuric acid and concentrated nitric acid to the halogenated benzene represented by formula (III).

Among the above, a method in which the nitration is performed by adding fuming sulfuric acid and fuming nitric acid to the halogenated benzene represented by formula (III), and a method in which the nitration is performed by adding fuming sulfuric acid and concentrated nitric acid to the halogenated benzene represented by formula (III) are particularly preferred.

The concentration of the concentrated nitric acid is preferably at least 65%, and the concentration of the concentrated sulfuric acid is preferably at least 90%.

The nitrate salt is preferably lithium nitrate, sodium nitrate, potassium nitrate, cesium nitrate, calcium nitrate or ammonium nitrate, and is more preferably sodium nitrate or potassium nitrate.

The reaction temperature is preferably at least −20° C. but not more than 150° C., more preferably greater than 0° C. but not more than 90° C., and still more preferably at least 20° C. but not more than 70° C.

Alternatively, a solvent that is inert to the nitration, such as methylene chloride or n-hexane, may be used if necessary.

The third step is a step of reducing the halogenated nitrobenzene represented by formula (II) to produce a halogenated aniline represented by formula (I).

The third step is performed by a hydrogenation using a reduction catalyst. Examples of the reduction catalyst include Pd, Pt, Ni and Rh. Among these, Pd is preferred.

The amount used of the catalyst, calculated as a mass of the metal relative to the mass of the 2,3-difluoro-5,6-dihalogenonitrobenzene, is preferably from 0.01 to 2.5% by mass, and more preferably from 0.1 to 1% by mass.

The reaction temperature is preferably from 0 to 150° C., more preferably from 10 to 100° C., and still more preferably from 40 to 70° C. The reaction pressure may be either normal pressure or an applied pressure, and is preferably within a range from 0 to 50 kg/cm².

The reaction solvent is preferably a solvent that is inert to the hydrogenation reaction, and examples include lower alcohols such as methyl alcohol and ethyl alcohol, ethers such as tetrahydrofuran and dioxane, hydrocarbons such as hexane and toluene, esters such as ethyl acetate, water, and mixtures of these solvents. An acid such as acetic acid or hydrochloric acid may be added to the solvent. Further, a method using a typical Bechamp reduction may also be used.

By using the method for producing a halogenated aniline according to the present invention, a halogenated aniline represented by formula (I) can be produced cheaply, easily and in large quantities, using 1,2-difluorobenzene or a 1-halogeno-3,4-difluorobenzene as the starting raw material.

Further, the thus obtained halogenated aniline represented by formula (I) may or may not be isolated before supply to the dehalogenation reaction described below.

By subjecting the obtained halogenated aniline represented by formula (I) to a dehalogenation reaction, 2,3-difluoroaniline can be produced in high yield.

This dehalogenation reaction is performed by using a reduction catalyst to effect a hydrogenation. A base such as triethylamine or caustic soda may also be added during this reaction.

The 2,3-difluoroaniline can be used as a production raw material for 2-[2-fluoro-6-(7,8-difluoro-2-methylquinolin-3-yloxy)phenyl]propan-2-ol and 2-[2-fluoro-6-(7,8-difluoroquinolin-3-yloxy)phenyl]propan-2-ol, which are known agricultural and horticultural germicides.

EXAMPLES

The present invention is described below in further detail using a series of examples. However, the present invention is in no way limited by these examples. Compounds of the present invention obtained in the following examples were isolated and purified, and the structural formulas of the compounds were then identified by elemental analysis, NMR data analysis and melting point measurement, thereby confirming the compounds as novel compounds.

Example 1

Production of 1,2-dichloro-4,5-difluorobenzene

First, 60.3 g (528.4 mmol) of 1,2-difluorobenzene and 1.0 g of anhydrous ferric chloride were mixed, and with the mixture undergoing constant stirring, 178.3 g (2.51 mol) of chlorine gas was introduced into the mixture over a period of 9 hours. During this period, the reaction temperature was maintained between 48 and 54° C. The reaction system was then deaerated by flushing with nitrogen. Subsequently, 40 mL of dichloromethane and 50 mL of water were added to the reaction mixture, and a phase separation was performed. The water layer was extracted with dichloromethane. The organic layers were combined and washed with a saturated aqueous solution of sodium sulfite. Quantitative analysis of the organic layer by HPLC revealed that the yield of 1,2-dichloro-4,5-difluorobenzene was 63.3% (61.20 g, 334.5 mmol).

Example 2

Production of 1,2-dibromo-4,5-difluorobenzene

First, 11.41 g (100 mmol) of 1,2-difluorobenzene, 31.47 g (110 mmol) of 1,3-dibromo-5,5-dimethylhydantoin and 62.30 g of acetic acid were mixed, and the mixture was cooled to 10° C. Subsequently, 49.15 g of concentrated sulfuric acid was added to the mixture, and a reaction was performed at 50° C. for 2.3 hours. An additional 1.46 g (5.1 mmol) of 1,3-dibromo-5,5-dimethylhydantoin was then added, and the reaction was continued for 50 minutes. Subsequently, the reaction mixture was extracted into 100 mL of hexane. The target compound was extracted from the waste acid layer using two 100 mL samples of hexane. The organic layers were combined and washed twice with 50 mL samples of water, once with 50 mL of a saturated aqueous solution of sodium thiosulfate, twice with 20 mL samples of a 1 mol/L aqueous solution of sodium hydroxide, and then once with 50 mL of water. Subsequently, the organic layer was concentrated under reduced pressure, yielding 1,2-dibromo-4,5-difluorobenzene as a yellow oily substance in a yield of 74% (73.80 mmol).

Example 3

Production of 1,2-dibromo-4,5-difluorobenzene

[Chemical Formula 8]

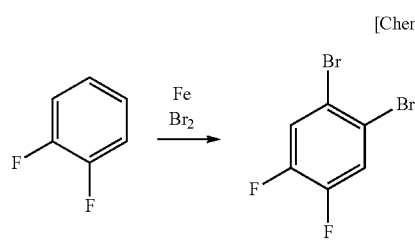

First, 84 mg (1.5 mmol) of iron powder was dispersed in 7.53 g (50 mmol) of 1,2-difluorobenzene, and the internal temperature was adjusted to 20° C. Subsequently, 18.4 g (115 mmol) of bromine was added dropwise over a period of 50 minutes. During this period, the internal temperature was maintained at about 20° C. Following the completion of the dropwise addition of bromine, the internal temperature was raised to 40° C., the mixture was reacted for 2 hours, and the internal temperature was then further raised to 50° C. and the reaction was continued for a further 2 hours. Following completion of the reaction, the reaction mixture was cooled to room temperature and poured into an aqueous solution prepared by dissolving 25.2 g of sodium bicarbonate and 12.6 g of sodium sulfite in 100 ml of water. The product was then extracted with ethyl acetate. The extracted solution was washed once with each of water and a saturated saline solution, and was then dried over magnesium sulfate. Following removal of the magnesium sulfate by filtration, quantitative analysis of the solution by HPLC revealed a reaction yield of 94% of the target product 1,2-dibromo-4,5-difluorobenzene.

Example 4

Production of 1-bromo-2-chloro-4,5-difluorobenzene

First, 14.86 g (100 mmol) of 4-chloro-1,2-difluorobenzene, 15.73 g (55 mmol) of 1,3-dibromo-5,5-dimethylhydantoin and 70 mL of acetic acid were mixed, and the mixture was cooled to 12° C. Subsequently, 30 mL of concentrated sulfuric acid was added to the mixture, and a reaction was performed at 50° C. for 1.7 hours. An additional 1.46 g (5.1 mmol) of 1,3-dibromo-5,5-dimethylhydantoin was then added, and the reaction was continued for 2 hours. Subsequently, the reaction mixture was extracted into 100 mL of hexane. The target compound was extracted from the waste acid layer using two 100 mL samples of hexane and then a further 30 mL of hexane. The organic layers were combined and washed twice with 50 mL samples of water, once with 50 mL of a saturated aqueous solution of sodium thiosulfate, twice with 20 mL samples of a 1 mol/L aqueous solution of sodium hydroxide, once with 30 mL of water, and then once with a saturated saline solution. Subsequently, the organic layer was concentrated under reduced pressure, yielding 17.36 g (yield: 76%) of 1-bromo-2-chloro-4,5-difluorobenzene as yellow crystals.

Example 5

Production of 1,2-dichloro-4,5-difluoro-3-nitrobenzene

First, 7.74 g (42.32 mmol) of 1,2-dichloro-4,5-difluorobenzene and 17.54 g of 30% by mass fuming sulfuric acid were mixed, and the mixture was heated to 20° C. Subsequently, 4.87 g (75.0 mmol) of 97% by mass fuming nitric acid was added dropwise to the mixture over a period of 2 hours with the temperature maintained at 20 to 26° C. Following completion of the dropwise addition, the resulting mixture was stirred at 20 to 26° C. for 2 hours. An additional 0.20 g (3.1 mmol) of 97% by mass fuming nitric acid was then added, and the resulting mixture was stirred for a further 3 hours. The reaction mixture was then poured into ice water and extracted into 50 mL of dichloromethane, and the water layer was then twice extracted with 20 mL samples of dichloromethane. The organic layers were combined, washed with water, and then concentrated under reduced pressure, yielding 1,2-dichloro-4,5-difluoro-3-nitrobenzene in a yield of 71%.

1,2-dichloro-4,5-difluoro-3-nitrobenzene:

$^1$H-NMR (400 MHz, CDCl$_3$): δ 7.56 (dd, 1H)

Example 6

Production of 1,2-dichloro-4,5-difluoro-3-nitrobenzene) (using potassium nitrate

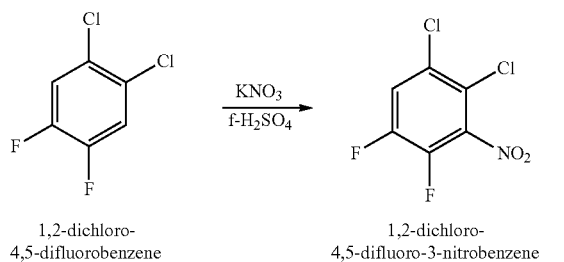

1,2-dichloro-4,5-difluorobenzene → 1,2-dichloro-4,5-difluoro-3-nitrobenzene

First, 1.83 g (10 mmol) of 1,2-dichloro-4,5-difluorobenzene was suspended in 5.6 mL of 30% by mass fuming sulfuric acid, and 2.02 g (20 mmol) of potassium nitrate was added gradually in small amounts to the suspension. A significant amount of heat was generated during this addition, and so the operation was performed under cooling in a water bath so that the internal temperature did not exceed 26° C. Following completion of the addition of the potassium nitrate, the reaction mixture was stirred for 2 hours. During this period, the internal temperature increased naturally to 35° C. Subsequently, the reaction mixture was poured onto ice, and the product was extracted with ethyl acetate. The resulting ethyl acetate solution was washed with water, and then with a saturated aqueous solution of sodium bicarbonate and a saturated saline solution, before being dried over magnesium sulfate. Quantitative analysis of the solution by HPLC revealed a yield of 31% of the target product 1,2-dichloro-4,5-difluoro-3-nitrobenzene.

Example 7

Production of 1,2-dibromo-4,5-difluoro-3-nitrobenzene

First, 6.80 g (25.0 mmol) of 1,2-dibromo-4,5-difluorobenzene and 18.54 g of 100% by mass sulfuric acid were mixed, and the resulting mixture was then heated to 50° C. A mixed acid prepared from 2.5 g (38.5 mmol) of 97% by mass fuming nitric acid and 9.30 g of 100% by mass sulfuric acid was then added dropwise to the mixture and reacted over a period of 130 minutes. The reaction temperature was maintained at 50 to 52° C. The resulting mixture was then poured into ice water, and 82.3 g of a 28% by mass aqueous solution of sodium hydroxide was added to neutralize the mixture. The precipitated crystals were collected by filtration. The filtrate was extracted with 200 mL of dichloromethane, the filtered crystals were also dissolved in this dichloromethane, and the resulting solution was concentrated under reduced pressure. The 6.21 g of the thus obtained crude crystals (crude yield: 78%) was recrystallized from a mixed solution of methanol and water, yielding 4.60 g (14.52 mmol, yield: 58%) of a yellowy white powder of 1,2-dibromo-4,5-difluoro-3-nitrobenzene.

1,2-dibromo-4,5-difluoro-3-nitrobenzene:
$^1$H-NMR (400 MHz, CDCl$_3$): δ 7.70 (dd, 1H)

Example 8

Production of 1,2-dibromo-4,5-difluoro-3-nitrobenzene) (using potassium nitrate

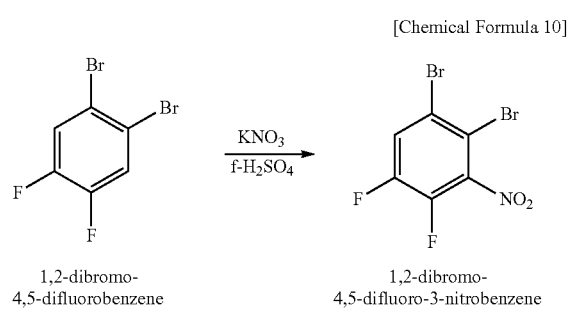

1,2-dibromo-4,5-difluorobenzene → 1,2-dibromo-4,5-difluoro-3-nitrobenzene

First, 2.71 g (10 mmol) of 1,2-dibromo-4,5-difluorobenzene was suspended in 5.6 mL of 30% by mass fuming sulfuric acid, and 2.02 g (20 mmol) of potassium nitrate was added gradually in small amounts to the suspension. A significant amount of heat was generated during this addition, and so the operation was performed under cooling in a water bath so that the internal temperature did not exceed 20° C. Following completion of the addition of the potassium nitrate, the internal temperature was raised to 35° C., and the reaction mixture was stirred for 2 hours 30 minutes, before being cooled to room temperature. Subsequently, the reaction mixture was poured onto ice, and the product was extracted with ethyl acetate. The resulting ethyl acetate solution was washed twice with water, and then with a saturated aqueous solution of sodium bicarbonate and a saturated saline solution, before being dried over magnesium sulfate. Quantitative analysis of the solution by HPLC revealed a yield of 41% of the target product 1,2-dibromo-4,5-difluoro-3-nitrobenzene.

Example 9

Production of 1,2-dibromo-4,5-difluoro-3-nitrobenzene) (using 90% nitric acid

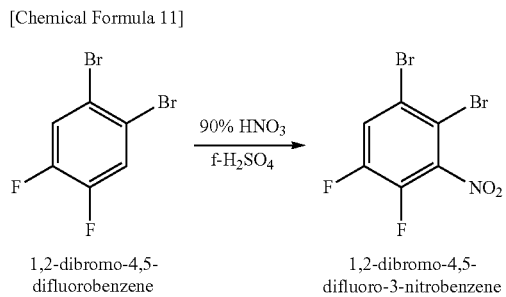 [SMILES: Fc1cc(Br)c(Br)cc1F ; O=[N+]([O-])c1c(F)c(F)cc(Br)c1Br]

1,2-dibromo-4,5-difluorobenzene → 1,2-dibromo-4,5-difluoro-3-nitrobenzene

First, 5.6 mL of 30% by mass fuming sulfuric acid was cooled to 5° C., and 1.05 g of 90% nitric acid (equivalent to 15 mmol of nitric acid) was then added gradually. Following completion of the addition, the temperature was raised to room temperature, and after stirring for 5 minutes, 2.71 g (10 mmol) of 1,2-dibromo-4,5-difluorobenzene was added. The temperature of the reaction mixture was raised to 35° C., the mixture was stirred for 1 hour 30 minutes, the temperature was then further raised to 45° C., and the mixture was stirred for a further 30 minutes, before being cooled to room temperature. The reaction mixture was poured onto ice, and the product was extracted with ethyl acetate. The resulting ethyl acetate solution was washed twice with water, and then with a saturated aqueous solution of sodium bicarbonate and a saturated saline solution, before being dried over magnesium sulfate and then concentrated. The thus obtained crude crystals were purified by silica gel column chromatography, yielding 2.91 g (9.18 mmol, yield: 92%) of the target product 1,2-dibromo-4,5-difluoro-3-nitrobenzene.

Example 10

Production of 1,2-dibromo-4,5-difluoro-3-nitrobenzene

[Chemical Formula 12]

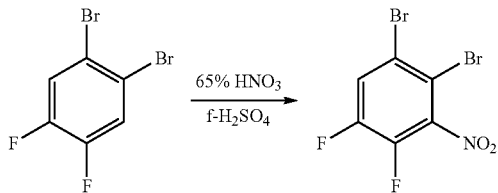

First, 8 mL of 30% by mass fuming sulfuric acid was cooled to 5° C., and 1.45 g of 65% nitric acid (equivalent to 15 mmol of nitric acid) was then added gradually. Following completion of the addition, the temperature was raised to room temperature, and after stirring for 5 minutes, 2.71 g (10 mmol) of 1,2-dibromo-4,5-difluorobenzene was added. The temperature of the reaction mixture was raised to 35° C., the mixture was stirred for 1 hour 30 minutes, and the temperature was then cooled to room temperature. The reaction mixture was poured onto ice, and the product was extracted with ethyl acetate. The resulting ethyl acetate solution was washed twice with water, and then with a saturated aqueous solution of sodium bicarbonate and a saturated saline solution, before being dried over magnesium sulfate. The magnesium sulfate was then removed by filtration, and quantitative analysis of the resulting solution by HPLC revealed a reaction yield of 94% of the target product 1,2-dibromo-4,5-difluoro-3-nitrobenzene.

Example 11

Production of 2,3-dichloro-5,6-difluoroaniline

First, 1.141 g (5.0 mmol) of 1,2-dichloro-4,5-difluoro-3-nitrobenzene was dissolved in a mixed solution of 5 mL of ethanol and 2.5 mL of water, and 0.8458 g (15.15 mmol) of iron powder and 0.5557 g (5.01 mmol) of calcium chloride were then added to the solution. The resulting mixture was heated to 60° C. and stirred for 1.3 hours. The mixture was then filtered, and the resulting filtrate was concentrated under reduced pressure, yielding 1.11 g of a brown-colored amorphous crude product. The crude product was purified by silica gel column chromatography, yielding 0.85 g (yield: 86%) of 2,3-dichloro-5,6-difluoroaniline as an orange-colored oily substance.

2,3-dichloro-5,6-difluoroaniline:
$^1$H-NMR (400 MHz, CDCl$_3$): δ 6.70 (dd, 1H), 4.36 (brs, 2H)

Example 12

Production of 2,3-dibromo-5,6-difluoroaniline

First, 1.57 g (4.95 mmol) of 1,2-dibromo-4,5-difluoro-3-nitrobenzene was dissolved in a mixed solution of 5 mL of ethanol and 2.5 mL of water, and 0.85 g (15.2 mmol) of iron powder and 0.54 g (4.87 mmol) of calcium chloride were then added to the solution. The resulting mixture was heated to 55° C. and stirred for 3.2 hours. The mixture was then filtered, and the resulting filtrate was concentrated under reduced pressure. The concentrate was purified by silica gel column chromatography, yielding 1.25 g (yield: 88%) of skin-colored crystals of 2,3-dibromo-5,6-difluoroaniline.

2,3-dibromo-5,6-difluoroaniline:
$^1$H-NMR (400 MHz, CDCl$_3$): δ 6.91 (dd, 1H), 4.45 (brs, 2H)

Example 13

Production of mixture of 3-bromo-2-chloro-5,6-difluoroaniline and 2-bromo-3-chloro-5,6-difluoroaniline First, 0.818 g (3.00 mmol) of a mixture of 1-bromo-2-chloro-4,5-difluoro-3-nitrobenzene and 2-bromo-1-chloro-4,5-difluoro-3-nitrobenzene (molar ratio 6:4) was dissolved in a mixed solution of 3 mL of ethanol and 1.5 mL of water, and 0.517 g (9.26 mmol) of iron powder and 0.335 g (3.02 mmol) of calcium chloride were then added to the solution. The resulting mixture was heated to 60° C. and stirred for 1.7 hours. The mixture was then filtered, the resulting filtrate was concentrated under reduced pressure, and the thus obtained crude product was purified by silica gel column chromatography, yielding 0.56 g (yield: 77%) of skin-colored crystals of a mixture of 3-bromo-2-chloro-5,6-difluoroaniline and 2-bromo-3-chloro-5,6-difluoroaniline (molar ratio 6:4).

3-bromo-2-chloro-5,6-difluoroaniline:
$^1$H-NMR (400 MHz, CDCl$_3$): δ 6.73 (dd, 1H)
2-bromo-3-chloro-5,6-difluoroaniline:
$^1$H-NMR (400 MHz, CDCl$_3$): δ 6.85 (dd, 1H)

Example 14

Production of 2,3-difluoroaniline

First, 0.506 g (1.76 mmol) of 2,3-dibromo-5,6-difluoroaniline was dissolved in 3.5 mL of methanol, and then 35.6 mg of 10% Pd/C (50% wet) and 0.722 g (7.05 mmol) of triethylamine were added. The atmosphere inside the reaction vessel was substituted with hydrogen, and the reaction mixture was reacted at 50° C. for 3 hours under slight hydrogen pressurization. Subsequently, the catalyst was removed by filtration. The resulting liquid was subjected to quantitative analysis by HPLC. The yield of 2,3-difluoroaniline was 98%.

Example 15

Production of 2,3-difluoroaniline

First, 1.147 g (5.03 mmol) of 1,2-dichloro-4,5-difluoro-3-nitrobenzene was dissolved in 10 mL of methanol, and then 100 mg of 10% Pd/C (50% wet) and 2.02 g (20.0 mmol) of triethylamine were added. The atmosphere inside the reaction vessel was substituted with hydrogen, and the reaction mixture was reacted at 45° C. for 2.8 hours under slight hydrogen pressurization. Analysis of the resulting reaction product by HPLC revealed 17.4 area % of 2,3-dichloro-5,6-difluoroaniline as a residual intermediate. Reaction was continued under the same conditions for a further 1.4 hours. The catalyst was then removed by filtration. The resulting liquid was subjected to quantitative analysis by HPLC. The yield of 2,3-difluoroaniline was 62%. The intermediate 2,3-dichloro-5,6-difluoroaniline existed in a residual amount of 6.4 area %.

Example 16

Production of 2,3-difluoroaniline

First, 0.638 g (2.01 mmol) of 1,2-dibromo-4,5-difluoro-3-nitrobenzene was dissolved in 4 mL of methanol, and then 48.4 mg of 10% Pd/C (50% wet) and 6.2 mg (0.06 mmol) of triethylamine were added. The atmosphere inside the reaction vessel was substituted with hydrogen, and the reaction mixture was reacted at 50° C. for 2 hours under slight hydrogen pressurization. Analysis of the resulting reaction product by HPLC revealed 2.2 area % of 2,3-dibromo-5,6-difluoroaniline as a residual intermediate. Reaction was continued under the same conditions for a further 0.5 hours. The catalyst was then removed by filtration. The resulting liquid was subjected to quantitative analysis by HPLC. The yield of 2,3-difluoroaniline was 93%. The intermediate 2,3-dibromo-5,6-difluoroaniline had been eliminated.

Example 17

Production of 2,3-difluoroaniline

First, 1.583 g (5.00 mmol) of 1,2-dibromo-4,5-difluoro-3-nitrobenzene was dissolved in 10 mL of methanol, and then 100 mg of 10% Pd/C (50% wet) and 2.03 g (20.1 mmol) of triethylamine were added. The atmosphere inside the reaction vessel was substituted with hydrogen, and the reaction mixture was reacted at 40° C. for 7 hours under slight hydrogen pressurization. Subsequently, the catalyst was removed by filtration. The resulting liquid was subjected to quantitative analysis by HPLC. The yield of the target product 2,3-difluoroaniline was 86%. The intermediate 2,3-dibromo-5,6-difluoroaniline had been eliminated.

Example 18

Production of 2,3-difluoroaniline

First, 0.953 g (4.19 mmol) of 1,2-dichloro-4,5-difluoro-3-nitrobenzene was dissolved in 10 mL of methanol, and then 115.7 mg of 10% Pd/C (47.40% wet) and 2.02 g (20.0 mmol) of triethylamine were added. The atmosphere inside the reaction vessel was substituted with hydrogen, and the reaction mixture was reacted at 40° C. for 2.0 hours under slight hydrogen pressurization. Subsequent analysis of the reaction mixture by HPLC revealed that the raw material 1,2-dichloro-4,5-difluoro-3-nitrobenzene had been eliminated. Reaction was continued under the same conditions for a further 0.7 hours. The catalyst was then removed by filtration. The resulting liquid was subjected to quantitative analysis by HPLC. The yield of 2,3-difluoroaniline was 52.4%. The intermediate 2,3-dichloro-5,6-difluoroaniline existed in a residual amount of 7.27 area %.

INDUSTRIAL APPLICABILITY

The halogenated aniline and the halogenated nitrobenzene according to the present invention are useful as production intermediates for 2,3-difluoroaniline. Moreover, 2,3-difluoroaniline is useful as a production intermediate for the active ingredients for agricultural and horticultural germicides such as 2-[2-fluoro-6-(7,8-difluoro-2-methylquinolin-3-yloxy)phenyl]propan-2-ol and 2-[2-fluoro-6-(7,8-difluoroquinolin-3-yloxy)phenyl]propan-2-ol.

The invention claimed is:

1. A halogenated aniline represented by formula (I):

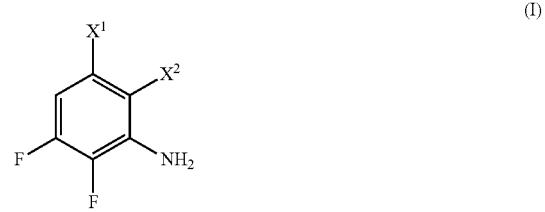

wherein each of $X^1$ and $X^2$ independently represents a chlorine atom, a bromine atom or an iodine atom.

2. A method for producing 2,3-difluoroaniline, comprising:

a step of halogenating 1,2-difluorobenzene or a 1-halogeno-3,4-difluorobenzene to obtain a halogenated benzene represented by formula (III):

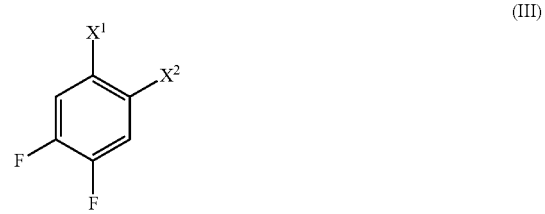

wherein each of $X^1$ and $X^2$ independently represents a chlorine atom, a bromine atom or an iodine atom, a step of nitrating the halogenated benzene to obtain a halogenated nitrobenzene represented by formula (II):

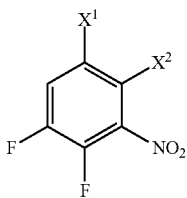

wherein each of $X^1$ and $X^2$ independently represents a chlorine atom, a bromine atom or an iodine atom,
  a step of reducing the halogenated nitrobenzene to obtain a halogenated aniline represented by formula (I):

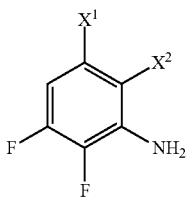

wherein each of $X^1$ and $X^2$ independently represents a chlorine atom, a bromine atom or an iodine atom, and
  a step of subsequently dehalogenating the halogenated aniline.

3. The method for producing 2,3-difluoroaniline according to claim 2, wherein the 1,2-difluorobenzene or 1-halogeno-3,4-difluorobenzene is halogenated using a Lewis acid catalyst.

4. A method for producing a halogenated aniline, comprising:
  a step of reducing a halogenated nitrobenzene represented by formula (II):

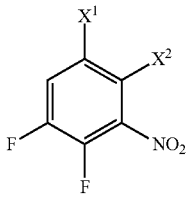

wherein each of $X^1$ and $X^2$ independently represents a chlorine atom, a bromine atom or an iodine atom, thereby obtaining a halogenated aniline represented by formula (I):

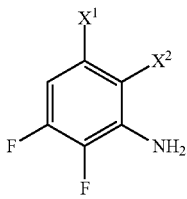

wherein each of $X^1$ and $X^2$ independently represents a chlorine atom, a bromine atom or an iodine atom.

5. A method for producing 2,3-difluoroaniline, comprising:
  a step of dehalogenating a halogenated aniline represented by formula (I):

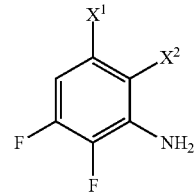

wherein each of $X^1$ and $X^2$ independently represents a chlorine atom, a bromine atom or an iodine atom.

6. A method for producing 2,3-difluoroaniline, comprising:
  a step of reducing a halogenated nitrobenzene represented by formula (II):

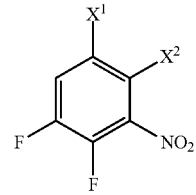

wherein each of $X^1$ and $X^2$ independently represents a chlorine atom, a bromine atom or an iodine atom, thereby obtaining a halogenated aniline represented by formula (I):

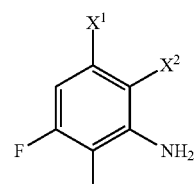

wherein each of $X^1$ and $X^2$ independently represents a chlorine atom, a bromine atom or an iodine atom, and
  a step of dehalogenating the halogenated aniline.

* * * * *